(12) United States Patent
Perkins et al.

(10) Patent No.: US 9,513,163 B2
(45) Date of Patent: Dec. 6, 2016

(54) OPTICAL DESIGN TECHNIQUES FOR MULTILAYER THIN FILM DEVICES IN COMPACT OPTICAL SYSTEMS

(71) Applicant: Halliburton Energy Services, Inc., Houston, TX (US)

(72) Inventors: David L. Perkins, The Woodlands, TX (US); Christopher Michael Jones, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 28 days.

(21) Appl. No.: 14/650,116

(22) PCT Filed: Jul. 28, 2014

(86) PCT No.: PCT/US2014/048370
§ 371 (c)(1),
(2) Date: Jun. 5, 2015

(87) PCT Pub. No.: WO2016/018206
PCT Pub. Date: Feb. 4, 2016

(65) Prior Publication Data
US 2016/0265971 A1    Sep. 15, 2016

(51) Int. Cl.
*G01N 21/25* (2006.01)
*G01J 3/02* (2006.01)
(Continued)

(52) U.S. Cl.
CPC ............ *G01J 3/0278* (2013.01); *G01N 21/31* (2013.01); *G02B 5/285* (2013.01); *G02B 27/0012* (2013.01)

(58) Field of Classification Search
CPC ........... G01J 3/02; G01J 3/0278; G01N 21/31; G01N 21/23; G01N 2201/0683; G02B 5/28; G02B 5/285; G02B 5/3083; G02B 27/00

See application file for complete search history.

(56) References Cited

U.S. PATENT DOCUMENTS 6,859,323 B1    2/2005   Gasloli
2004/0151629 A1*   8/2004   Pease ............... B01L 3/5027
                                                                                                  422/68.1

(Continued)

FOREIGN PATENT DOCUMENTS

KR       100892743 B1    4/2009
WO     2013162753 A1   10/2013
(Continued)

OTHER PUBLICATIONS

Extended European Search Report dated Apr. 12, 2016 for EP 14870640.1.

(Continued)

*Primary Examiner* — Abdullahi Nur
(74) *Attorney, Agent, or Firm* — McDermott Will & Emery LLP; Benjamin Fite

(57) ABSTRACT

Methods and systems for designing an integrated computational element (ICE) device are provided. The method includes generating a plurality of ICE device models with a design suite, each ICE device model being configured to detect a characteristic of interest of a sample, and including one or more layers. Further determining at least one transmission spectrum for each theoretical ICE device model for at least one distribution of incident light angles and at least one performance criteria for each ICE device model for the at least one of distribution of incident light angles. Also, ranking the ICE device model based on the at least one performance criteria of each ICE device model at the at least one distribution of incident light angles, and selecting for fabrication one or more ICE device models based on favor- (Continued)

able angular tolerance. An optical system including an ICE device as described above is also provided.

20 Claims, 9 Drawing Sheets

(51) Int. Cl.
*G02B 5/28* (2006.01)
*G02B 27/00* (2006.01)
*G01N 21/31* (2006.01)

(56) References Cited

U.S. PATENT DOCUMENTS

| | | |
|---|---|---|
| 2004/0265477 A1 | 12/2004 | Nabatova-Gabain et al. |
| 2010/0326955 A1 | 12/2010 | Gao et al. |
| 2013/0284904 A1 | 10/2013 | Freese et al. |

FOREIGN PATENT DOCUMENTS

| | | |
|---|---|---|
| WO | 2013162913 A1 | 10/2013 |
| WO | 2016018206 A1 | 2/2016 |

OTHER PUBLICATIONS

International Search Report and Written Opinion for PCT/US2014/048370 dated Apr. 15, 2015.
Soyemi et al., Design of Angle-Tolerant Multivariate Optical Elements for Chemical Imaging, Applied Optics, vol. 41, No. 10, pp. 1936-1941.
Simcock et al., Precision in Imaging Multivariate Optical Computing, Applied Optics, vol. 46, No. 7, pp. 1066-1080, 2007.

\* cited by examiner

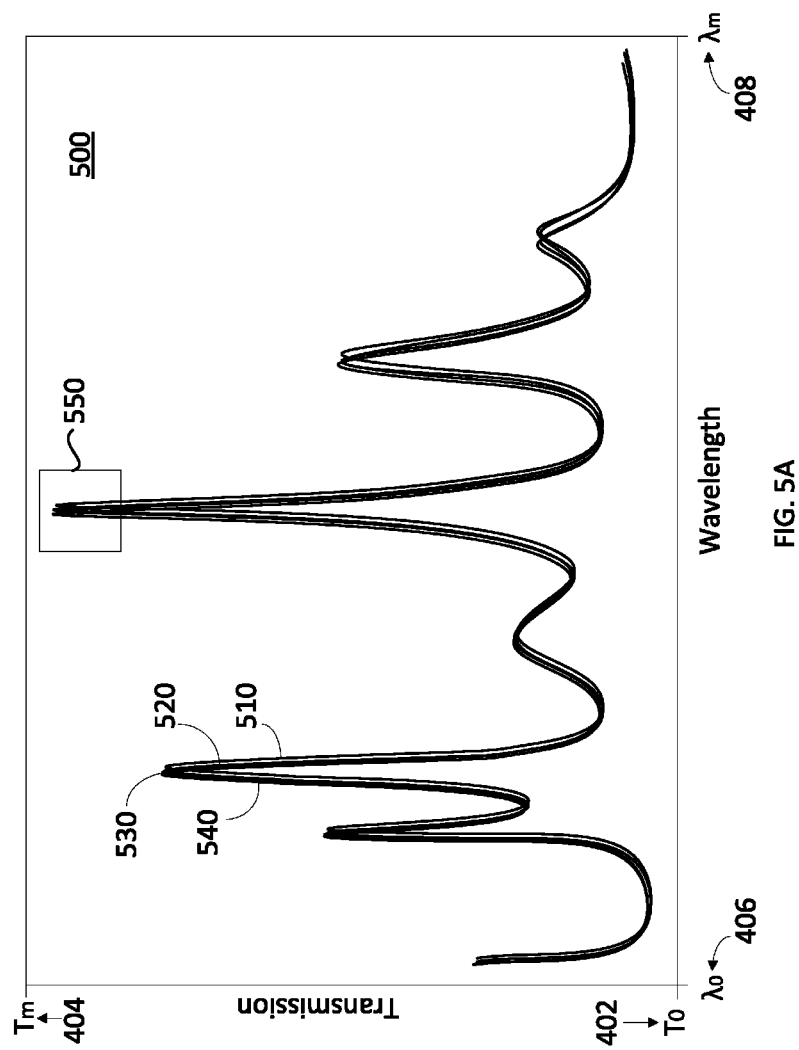

OPTICAL DESIGN TECHNIQUES FOR MULTILAYER THIN FILM DEVICES IN COMPACT OPTICAL SYSTEMS

BACKGROUND

The present disclosure relates to optical thin-film based Integrated Computational Element (ICE) devices and, more particularly, to design techniques that provide favorable characteristics for ICE devices used in compact optical systems.

Compact optical systems can include optical beams having a high numerical aperture (NA). Optical beams with high NA include a number of light rays having a broad distribution of angles of incidence on the surface of optical components (normal incidence). Multilayer optical thin films in state-of-the-art optical systems are designed for normal incidence of light rays (e.g., collimated optical beams). As a result, a shift in spectral properties is expected when the multilayer optical thin film is incorporated into a compact optical system. This shift may significantly affect measurement performance of the multilayer thin film and the compact optical system as a whole. Thus, multilayer optical thin films designed for collimated incident optical beams may be rendered unusable in compact optical systems, which are otherwise desirable for use in extreme environments.

Some attempts to solve the problem of incident optical beams with high NA include vignetting the optical beam by providing spatial filters that select light rays parallel to the optical axis (i.e., forming close to normal incidence on a multilayered thin film). This approach relieves the problem of spectral accuracy of the compact optical system. However, vignetting the optical beam substantially reduces the signal-to-noise ratio (SNR) at the photo detector, in detriment of system performance.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

FIG. 5A illustrates a plot of weighted spectra for optical beams having different angular distributions incident onto an exemplary ICE device, according to some embodiments.

DETAILED DESCRIPTION

Figure 1:
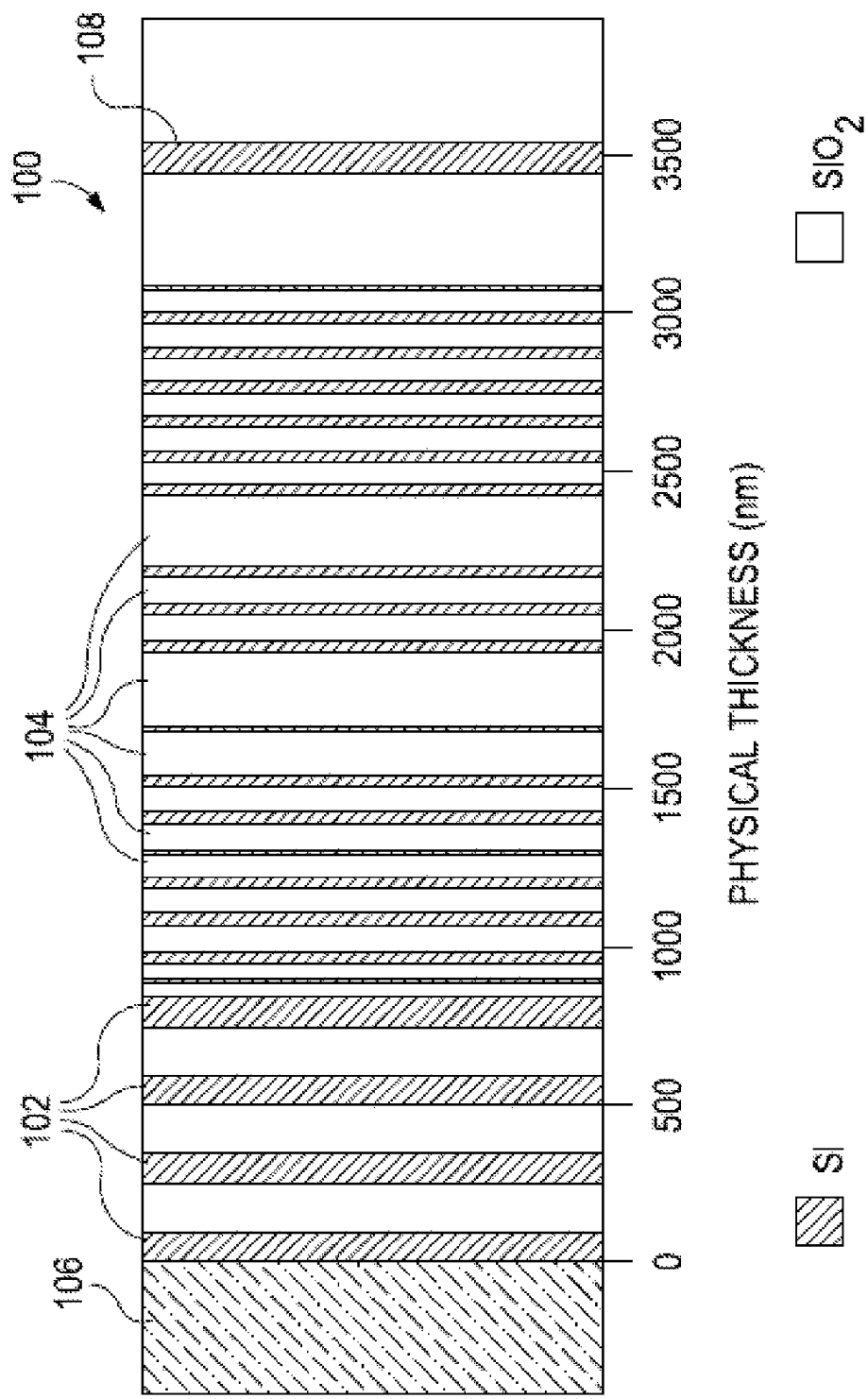
FIG. 1 illustrates an exemplary integrated computational element (ICE) device, according to one or more embodiments.

The present disclosure relates to optical thin-film based Integrated Computational Element (ICE) devices and, more particularly, to design techniques that provide favorable characteristics for optical elements used in compact optical systems.

As used herein, the term "characteristic" refers to a chemical, mechanical, or physical property of a substance. A characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be monitored with the optical computing devices described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc.), and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation associated with a substance and produce an output of electromagnetic radiation from a processing element arranged within the optical computing device. The processing element may be, for example, an integrated computational element (ICE), also known as a multivariate optical element (MOE). The electromagnetic radiation that optically interacts with the processing element is changed so as to be readable by a detector, such that an output of the detector can be correlated to a particular characteristic of the substance. The output of electromagnetic radiation from the processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by optical computing devices.

As used herein, the term "optically interact" or variations thereof refers to the reflection, transmission, scattering, diffraction, or absorption of electromagnetic radiation either on, through, or from one or more processing elements (i.e., ICE or MOE components) or a substance being analyzed by the processing elements. Accordingly, optically interacted light refers to electromagnetic radiation that has been reflected, transmitted, scattered, diffracted, or absorbed by, emitted, or re-radiated, for example, using a processing element, but may also apply to interaction with a substance.

As mentioned above, the processing element used in the above-defined optical computing devices may be an integrated computational element (ICE) device. In operation, an ICE device is capable of distinguishing electromagnetic radiation related to a characteristic of interest of a substance from electromagnetic radiation related to other components of the substance.

Embodiments disclosed herein provide ICE devices that are optimized for compact optical systems. A compact optical system includes short optical paths having high incident angles on the ICE device. Miniaturized optical systems using ICE devices (i.e., micro-ICE optical probe) are an example of compact optical systems as disclosed herein. Micro-ICE systems result in shorter optical paths than those of traditional optical systems using ICE devices. Shorter optical paths can include non-collimated optical beams, or optical beams having a high NA. The methods and systems disclosed herein may prove useful in reducing the prediction errors associated with high angles of incident light onto the ICE device in such compact optical systems.

Compact optical systems as disclosed herein are used to analyze and monitor a substance in real time in extreme environments. A compact optical system having reduced dimensions may be disposed in a remote location and be subject to high pressure, high temperature, vibrations and shock. An example of such an environment may be the downhole in an oil exploration or extraction platform. With the reduced dimensions of a compact optical system, it is desirable to have short optical paths while maintaining relatively large optical sources, detectors, and optical beams. Larger optical sources and detectors with larger optical beams are desirable to maintain and enhance signal-to-noise ratio (SNR) even for a reduced size compact optical system. More generally, compact optical sources providing relevant SNR tend to have optical beams with high NA. High NA optical beams include a plurality of light rays propagating at wide angles relative to a chief ray propagating along the optical axis of an optical assembly. More specifically, high NA beams include a plurality of light rays having a distribution of angles of incidence on the surface of an optical element such as an ICE device. The angle of incidence of a light ray is measured relative to a normal of a contact surface between the light ray and the optical element (e.g., the ICE device).

Compact optical systems consistent with the present disclosure include a processing element that optically interacts with a substance to determine quantitative and/or qualitative values of one or more physical or chemical properties of the substance. The processing element may be, for example, an ICE device, also known as a multivariate optical element (MOE), which is an optical interference filter that can be designed to operate over a continuum of wavelengths in the electromagnetic spectrum from the UV to mid-infrared (MIR) ranges, or any sub-set of that region. Electromagnetic radiation that optically interacts with the ICE device is changed so as to be readable by a detector, such that an output of the detector can be correlated to the physical or chemical property of the substance being analyzed. Embodiments as disclosed herein include ICE devices designed to operate with incident electromagnetic radiation forming high NA beams.

The present disclosure facilitates the evaluation of desired ICE devices to determine the effect of a high NA incident optical beam on chemometric predictability. In addition to determining a mean squared error (MSE) from the spectral changes of the ICE device, the present disclosure uses a standard error of calibration (SEC) for chemometric measurements using the ICE device. As a result, methods disclosed herein may determine ICE device models that are robust with respect to the NA of an optical beam in a compact optical system. Methods disclosed herein may help an operator determine when an ICE device model performs within a desirable SEC in a compact optical system. Moreover, using the methods disclosed herein, an operator might intelligently determine a desirable batch of ICE device models based on a lower batch-averaged SEC.

The disclosed systems and methods may be suitable for designing, evaluating, and fabricating ICE devices for use in the oil and gas industry. Oil and gas industries may deploy compact optical systems as disclosed herein for exploration and extraction of hydrocarbons under extreme conditions and environments. It will be appreciated, however, that the systems and methods disclosed herein are equally applicable to the design and fabrication of compact optical systems used in other fields. For instance, compact optical systems consistent with the present disclosure may be applied in the food and drug industry, industrial applications, mining industries, or any field where it may be advantageous to determine in real-time or near real-time a characteristic of a specific substance, but where environmental factors, such as temperature, pressure, humidity, vibrations and shock may have a critical impact.

Referring to FIG. 1, illustrated is an exemplary ICE device 100, according to one or more embodiments. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples of materials might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation, and may be able to detect a sample substance. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths. It should be understood that the exemplary ICE 100 in FIG. 1 does not in fact represent any particular characteristic of a given substance, but is provided for purposes of illustration only. Consequently, the number of layers 102, 104 and their relative thicknesses, as shown in FIG. 1, bear no correlation to any particular characteristic. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the given substance being analyzed.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The ICE 100 may be configured to perform the dot product of the electromagnetic radiation received by the ICE 100 and the wavelength dependent transmission function of the ICE 100. The wavelength dependent transmission function of the ICE 100 is dependent on the layer material refractive index, the number of layers 102, 104 and the layer thicknesses. The ICE 100 transmission function is then analogous to a desired regression vector derived from the solution to a linear multivariate problem targeting a specific component of the sample being analyzed. As a result, the output light intensity of the ICE 100 is related to the characteristic or analyte of interest.

Optical computing devices employing such an ICE 100 may be capable of extracting the information of the spectral fingerprint of multiple characteristics or analytes within a substance and converting that information into a detectable output regarding the overall properties of the substance. That is, through suitable configurations of the optical computing devices, electromagnetic radiation associated with characteristics or analytes of interest in a substance can be separated from electromagnetic radiation associated with all other components of the substance in order to estimate the properties of the substance in real-time or near real-time. Accordingly, ICE device 100 is able to distinguish and process electromagnetic radiation related to a characteristic or analyte of interest.

Before the ICE device 100 is physically fabricated, one or more ICE device models are typically generated. Such models may be generated using, for example, a computer-based software program or design suite that may be stored on a computer-readable medium containing program instructions configured to be executed by one or more processors of a computer system. The design suite may be configured to generate several ICE device models, each being configured or otherwise adapted to detect a particular characteristic or analyte of interest.

ICE device models may be calculated using weighted averages of incident angles representing a plurality of angular distributions for an incoming optical beam. The results from the plurality of angular distributions become a basis for comparing different ICE device models based on performance criteria. Such performance criteria may include, but are not limited to, minimum prediction error, standard error of calibration (SEC), standard error of performance (SEP), sensitivity, slope of the calibration curve, signal-to-noise ratio (SNR), and mean transmission value corresponding to the particular characteristic or analyte of interest.

Once the ICE device models are generated, they may be sorted by the design suite based on, for example, prediction error and signal. In some cases, various ICE device models may be sorted based on their overall SEC (i.e., chemometric predictability) as tested against a known value for the characteristic or analyte of interest. For example, the SEC for each ICE device model may be calculated by taking the square root of the sum of squares between the known value for the analyte of interest and the predicted value as derived from the transmission spectrum of the ICE device model. This is accomplished for each ICE device model by calculating its respective transmission spectrum and applying that transmission spectrum to the known data set of the analyte of interest. More generally, the ICE device model may be evaluated based on its reflection spectrum, or even based on a diffraction pattern associated with it.

In some embodiments, the design suite may further be configured to iterate and/or optimize layer thicknesses and layer number until reaching a reasonable SEC for one or more of the theoretical ICE device models. The resulting SEC for each ICE device model is indicative of how good of a predictor the particular ICE device will be for the analyte of interest. In some embodiments, ICE device models exhibiting a SEC of 2.00 or less, for example, may be considered "predictive" and ICE device models exhibiting a SEC of greater than 2.00 may be considered "non-predictive." In other embodiments, the resulting SEC value that determines whether an ICE device model is considered predictive or not may be greater or less than 2.00, without departing from the scope of the disclosure. ICE device models considered non-predictive may be removed from consideration by an operator, or by software instructions carried out by the design suite.

Once a predictive or desired ICE device model is selected for fabrication, the model is loaded into a fabrication computer program configured to instruct a fabrication machine or module to physically create the ICE device. Similar to the design suite, the fabrication computer program software may be stored on a computer-readable medium containing program instructions configured to be executed by one or more processors of a computer system. The fabrication computer program may be configured to receive or otherwise download the specifications for the desired ICE model, as generated by the design suite, and physically create a corresponding ICE device by methodically depositing the various layers of the ICE device to the specified layer thicknesses.

Figure 2:
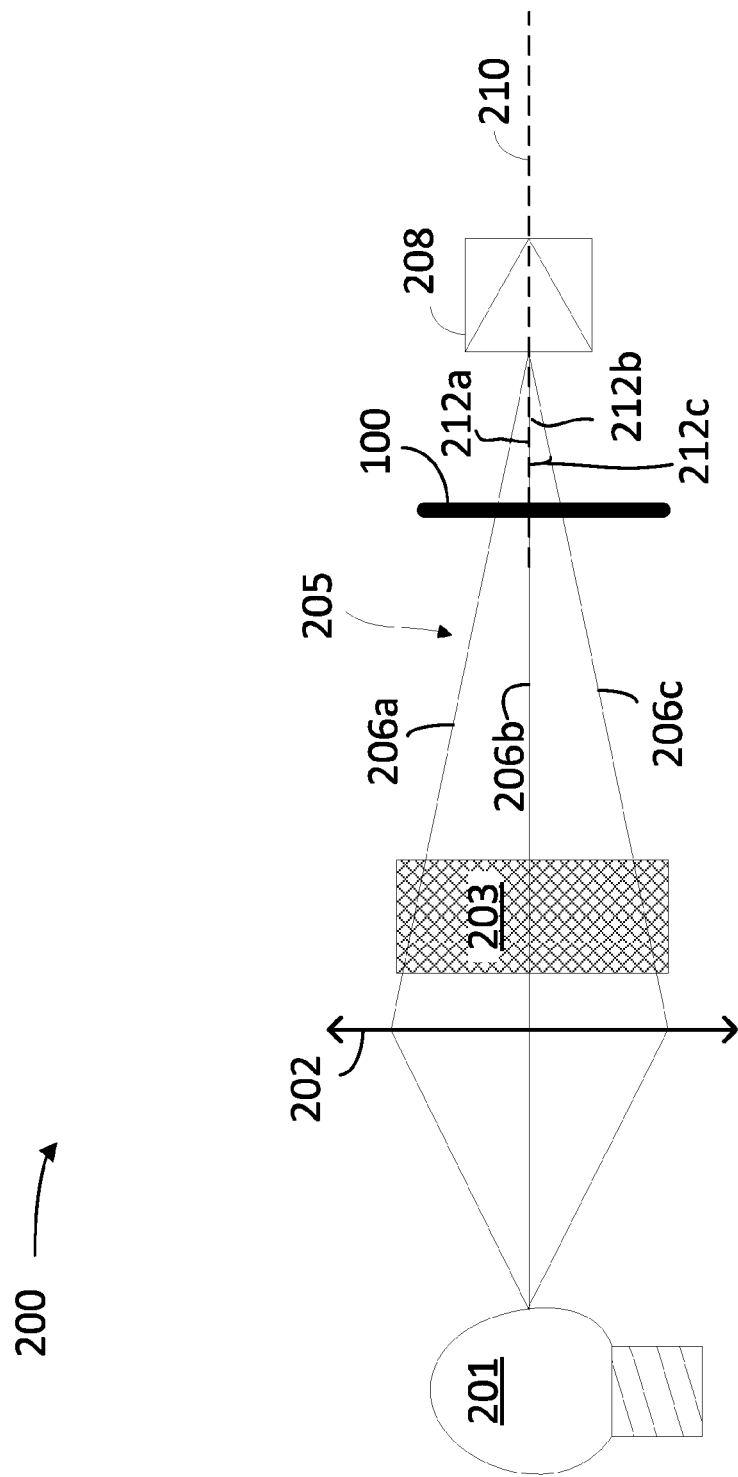
FIG. 2 illustrates an optical system including a high NA optical beam, according to some embodiments.

FIG. 2 illustrates an optical system 200 including a high NA optical beam, according to one or more embodiments of the present disclosure. In some embodiments, optical system 200 may be a compact optical system such as a Micro-ICE optical probe, and may employ the ICE device 100 generally described above. A light source 201 generates light that an optical assembly 202 forms into an optical beam 205 interacting with a sample 203 of a substance. Optical assembly 202 directs optical beam 205 onto a detector 208. Detector 208 is configured to provide an electrical signal in response to an intensity of light in the spectral bandwidth of the light generated by optical source 201. Accordingly, optical assembly 202 may include a lens, an aspheric lens, a diffractive element, a Fresnel lens, a collimator, a mirror, a prism, or any combination of the above. Optical beam 205 includes light rays 206a, 206b, and 206c (hereinafter referred to collectively as 'light rays 206') impinging on ICE device 100. Light ray 206b may be a chief ray propagating through the optical axis of optical assembly 202. A surface normal 210 defines the orientation of a contact surface between ICE device 100 and light rays 206 in optical beam 205. Light ray 206a forms an incidence angle 212a with normal 210, and light ray 206c forms an incidence angle 212c with normal 210. In the illustrated embodiment, light ray 206b forms an incidence angle 212b of zero with surface normal 210, but other configurations may allow for this angle to be non-zero, thereby exhibiting an overall 'tilt' of ICE device 100 relative to the optical axis of optical assembly 202. Hereinafter, incidence angles 212a, 212b, and 212c will be referred to collectively as incidence angles 212.

A size reduction of ICE device 100 to fit with smaller size constraints (i.e., the micro-ICE optical probe) results in a much smaller optical path and optical beam 205 having a larger NA. At the same time, some of the optical components (i.e., light source 201 and detector 208) may not scale down in size together with the optical system. In fact, in some embodiments, it is desirable to at least maintain the size of the light source 201 and the detector 208 as the optical system is miniaturized to maintain or enhance the SNR. This results in less than full light collimation and higher incidence angles 212 than are considered in design and fabrication of ICE device 100. A higher proportion of incident light rays with non-zero incidence angles 212 can lead to reduced accuracy of the measurements made with ICE device 100. Because of the possibility of higher angles and optical aberrations, it is desirable to design ICE device 100 to be robust with respect to angle. For example, in some embodiments optical assembly 202 includes aspheric elements incorporating broadly spread angular distributions.

While optical system 200 has been described in the context of a compact optical system such as a Micro-ICE system, larger optical systems are also consistent with FIG. 2. For example, optical system 200 may include aspheric elements for high optical throughput and may also include high NA optical beams. In such configurations, optical system 200 may be large in size (e.g., as compared to a Micro-ICE system). In some embodiments, ICE device 100 may be in contact with the sensing surface of detector 208. For example, in some embodiments ICE device 100 may be deposited directly on the detector when the detector is able to withstand temperatures and other environmental conditions of the ICE device deposition process. Further, according to some embodiments, ICE device 100 may be formed into a curved surface with respect to optical beam 205. In some embodiments, ICE device 100 may be deposited on the surface of an optical element in optical assembly 202. More particularly, in some embodiments ICE device 100 may be deposited on a surface of a lens, such as an aspheric lens. In that regard, even for a perfectly collimated optical beam 205 impinging on ICE device 100 (NA=0), in some embodiments incidence angle 212 may form a broad distribution on ICE device 100. For example, this may be the case when the ICE device is deposited on a high NA optical element (e.g., an aspheric lens).

Figure 3:
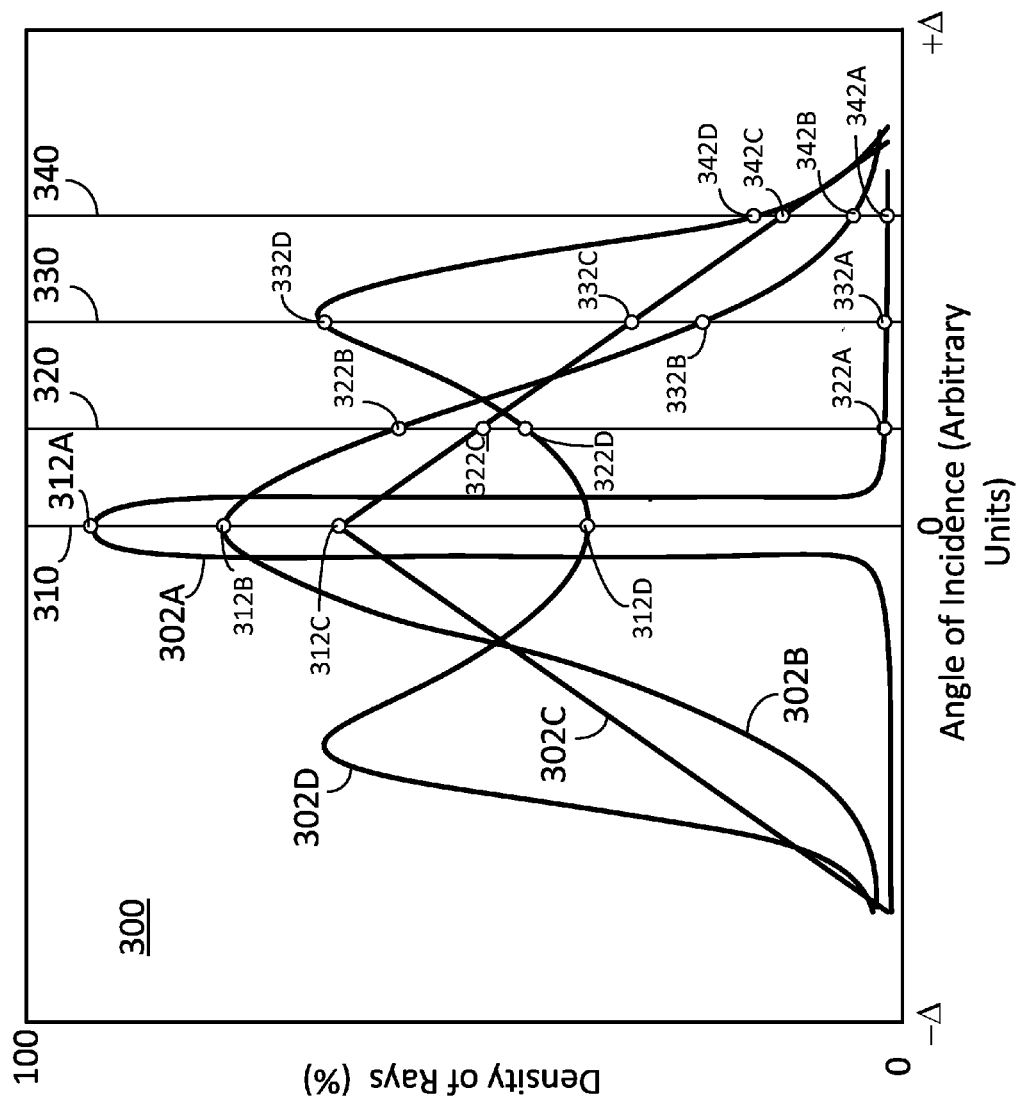
FIG. 3 illustrates a plot with a plurality of angular distributions for the rays in an optical beam, according to some embodiments.

Referring now to FIG. 3, with continued reference to FIG. 2, illustrated is a plot 300 with a plurality of angular distributions 302A, 302B, 302C, and 302D for light rays 206 in optical beam 205 according to some embodiments. Angular distributions 302A, 302B, 302C, and 302D will be collectively referred to hereinafter as "angular distributions 302." The abscissa (X-axis) in plot 300 indicates the angle of incidence of a light ray onto the ICE device surface. The angle of incidence is measured with respect to a normal direction to the ICE device surface (cf. FIG. 2). The ordinate (Y-axis) in plot 300 indicates a 'density of rays' for a given angle of incidence. A density of rays may be a number of rays having a given angle of incidence per unit area of the contact surface. In some embodiments, a density of rays may represent a percent of the total number of light rays impinging on a contact surface of the ICE device. The percent of rays within the optical beam have a given angle of incidence. Accordingly, the ordinate of a point in plot 300 indicates a percent of incident light at each angle in the abscissa.

In angular distribution 302A, almost all light rays incident on the ICE device have near normal incidence, close to an ideally collimated optical beam. In angular distribution 302B, a normal distribution function is used. In angular distribution 302C, a triangular distribution function is used, and angular distribution 302D is a bimodal distribution function. Angular distributions 302 represent increasing amounts of light rays incident at larger angles. Accordingly, angular distributions 302B, 302C, and 302D may correspond to a high NA optical beam in a compact optical system. Areas under each angular distribution 302 are normalized to the total optical beam intensity (100% in FIG. 3). While a high NA optical beam may have any of angular distributions 302B, 302C, and 302D, other angular distributions may be possible in the context of the present disclosure. In some embodiments, angular distributions 302B, 302C, and 302D may represent incident rays from optical beam 205 onto an ICE device deposited on a curved surface.

FIG. 3 illustrates angles of incidence 310, 320, 330, and 340 in increasing order. One of ordinary skill will recognize that the specific value of angles of incidence 310, 320, 330, and 340 is not limiting to the embodiments consistent with the present disclosure. For example, angle of incidence 310 may be close to a normal incidence, or zero. Likewise, angle of incidence 320 may be about 5° from normal incidence. Angle of incidence 330 may be around 10° from normal incidence, and angle of incidence 340 may be about 15° from normal incidence.

Point 312A indicates a percentage of light rays in an optical beam with angular distribution 302A having an angle of incidence 310. Point 312B indicates a percentage of light rays in an optical beam with angular distribution 302B having angle of incidence 310. Point 312C indicates a percentage of light rays in an optical beam with angular distribution 302C having angle of incidence 310, and point 312D indicates a percentage of light rays in an optical beam with angular distribution 302D having angle of incidence 310. Likewise, point 322A indicates a percentage of light rays in an optical beam with angular distribution 302A having angle of incidence 320, point 322B indicates a percentage of light rays in an optical beam with angular distribution 302B having angle of incidence 320, point 322C indicates a percentage of light rays in an optical beam with angular distribution 302C having angle of incidence 320, and point 322D indicates a percentage of light rays in an optical beam with angular distribution 302D having angle of incidence 320. Accordingly, an optical beam with angular distribution 302A may include about 0% light rays at angle 330 (point 332A). An optical beam with angular distribution 302B may include about 1.1% light rays incident at angle 330 (point 332B). An optical beam with angular distribution 302C may include about 2.5% light rays incident at angle 330 (point 332C), and an optical beam with angular distribution 302D may include about 7.0% light rays incident at angle 330 (point 332D). Point 342A indicates a percentage of light rays in an optical beam with angular distribution 302A having angle of incidence 340. Point 342B indicates a percentage of light rays in an optical beam with angular distribution 302B having angle of incidence 340. Point 342C indicates a percentage of light rays in an optical beam with angular distribution 302C having angle of incidence 340, and point 342D indicates a percentage of light rays in an optical beam with angular distribution 302D having angle of incidence 340.

Angular distributions 302A-D are symmetric about zero (normal incidence), indicating an axi-symmetric optical beam 205. More generally, angular distributions consistent with the present disclosure may be symmetrical about an incidence angle different from zero (e.g., when a flat ICE device 100 is tilted at a non-zero angle relative to optical beam 205). Further, angular distributions consistent with the present disclosure may not be symmetric about the abscissae in FIG. 3 (e.g., when optical beam 205 includes a coma aberration, as one of ordinary skill will recognize).

Figure 4A:
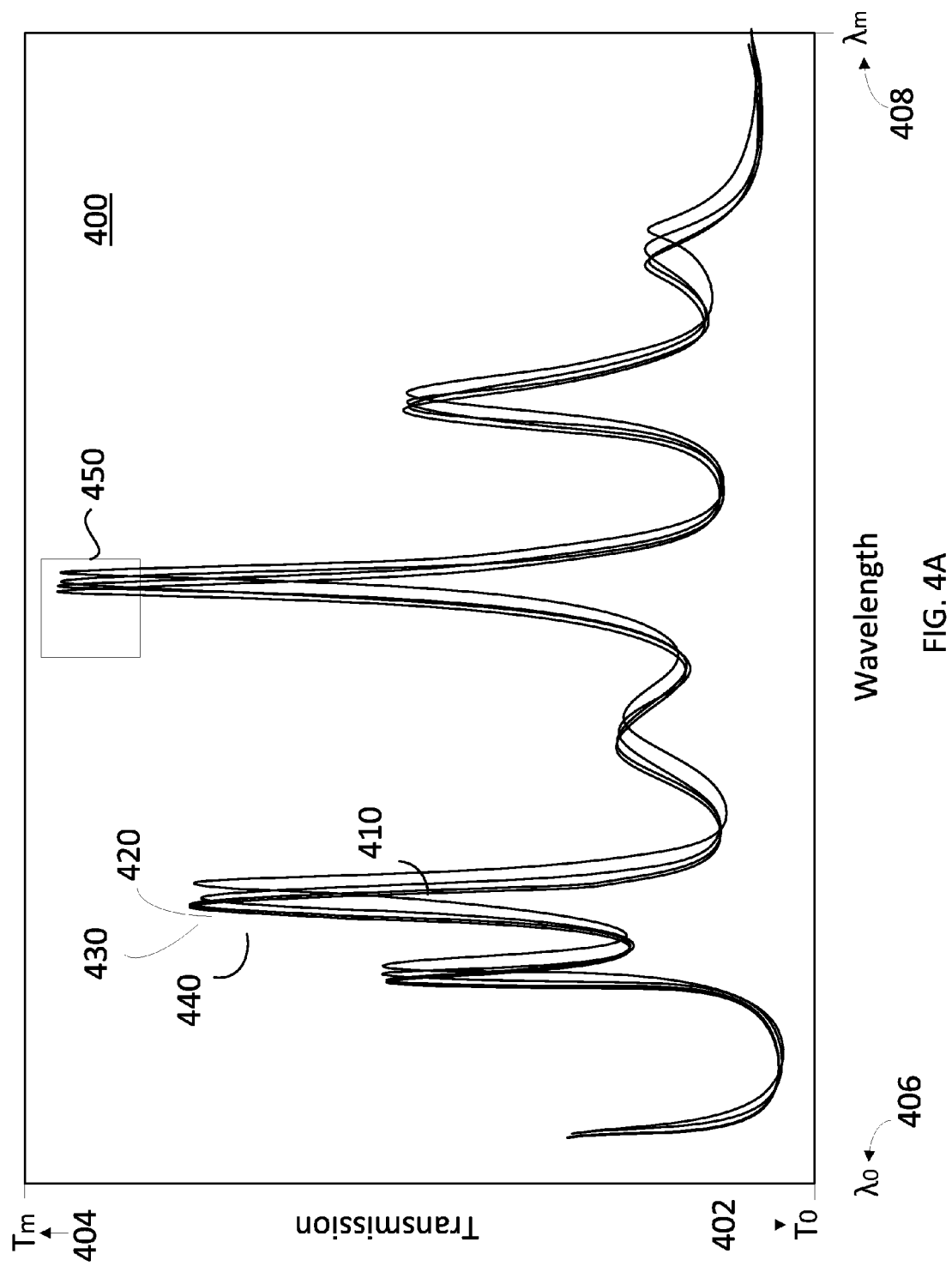
FIG. 4A illustrates a plot depicting transmission spectra for collimated beams at different angles of incidence on an ICE device, according to some embodiments.

FIG. 4A illustrates a plot 400 depicting transmission spectra for collimated beams at different angles of incidence on ICE device 100, according to some embodiments. The transmission spectra illustrated in FIG. 4A corresponds to an ICE device modeled for the measurement of ethane. Without loss of generality, one of ordinary skill will recognize that ICE device spectra in FIG. 4A may be associated with any characteristic of a sample under analysis other than, or including, ethane. The plot 400 shows wavelength in the abscissae and transmission coefficient in the ordinates. Transmission coefficient in plot 400 may span a range from a minimum value, $T_o$ 402, to a maximum value, $T_m$ 404. Accordingly, $T_0$ 402 may be zero and $T_m$ 404 may be one (1.0). Wavelength in plot 400 may span a range from a minimum value, $\lambda_o$ 406, to a maximum value, $\lambda_m$ 408. Without loss of generality, the transmission spectra illustrated in plot 400 includes a wavelength range spanning from $\lambda_o$ 406 of about 1500 nm to $\lambda_m$ 408 of about 2500 nm. More generally, plot 400 may refer to reflection spectra, or even a diffraction pattern according to some embodiments.

With continued reference to FIG. 3, spectrum 410 corresponds to ICE device transmission for light rays at incidence angle 310 of FIG. 3. Spectrum 420 corresponds to ICE device transmission for light rays at incidence angle 320 of FIG. 3. Spectrum 430 corresponds to ICE device transmission for light rays at incidence angle 330 of FIG. 3, and Spectrum 440 corresponds to ICE device transmission for light rays at incidence angle 340 of FIG. 3. More generally, as the incidence angle of a light ray increases relative to the normal of an ICE device, the transmission spectrum shifts towards shorter wavelengths (e.g., "blue shift").

Figure 4B:
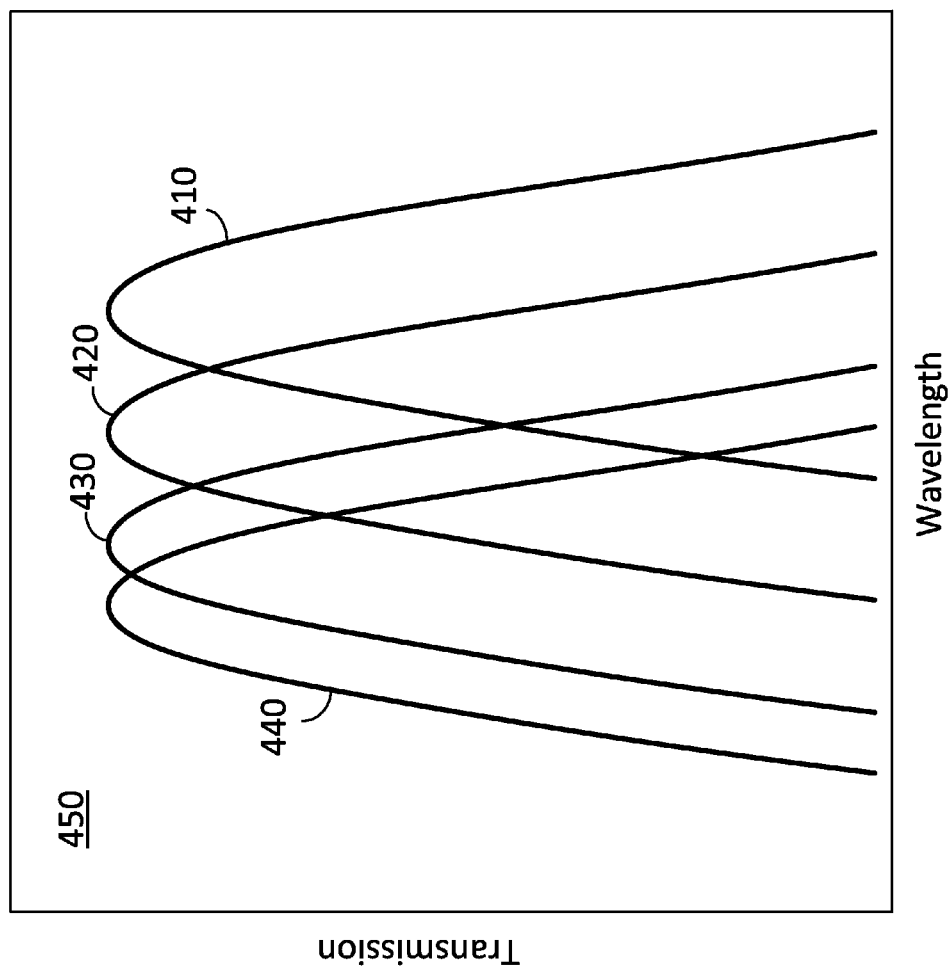
FIG. 4B illustrates a detailed view of a peak in the transmission spectra of FIG. 4A, according to some embodiments.

Referring to FIG. 4B, illustrated is an enlarged view of a peak 450 depicted in the transmission spectra of the plot 400, according to some embodiments. Accordingly, ordinates and abscissae in FIG. 4B are as described above in relation to plot 400. Peak 450 is generally centered at about 2012 nanometers (in ethane), detailing the magnitude of the spectral shift. A small blue shift occurs with a tilt from incidence angle 310 (near normal incidence) to incidence angle 320 (at about 5°). A larger blue shift occurs with a tilt from incidence angle 310 to incidence angle 330 (at about 10°), and even a larger blue shift occurs with a tilt from incidence angle 310 to incidence angle 340 (at about) 15°. Spectra 410, 420, 430, and 440 are used to determine weighted spectra for an ICE device according to the angular distribution corresponding to a selected optical beam.

FIG. 5A illustrates a plot 500 of weighted spectra 510, 520, 530, and 540, for optical beams having different angular distributions incident onto an exemplary ICE device, according to some embodiments. Accordingly, ICE device 100 in FIG. 5A may be the ethane ICE device of FIGS. 4A-4B. Weighted spectrum 510 corresponds to an incident optical beam having angular distribution 302A, on the ICE device of FIGS. 4A-B. Weighted spectrum 520 corresponds to an incident optical beam having angular distribution 302B, on the ICE device. Weighted spectrum 530 corresponds to an incident optical beam having angular distribution 302C, on the ICE device. Weighted spectrum 540 corresponds to an incident optical beam having angular distribution 302D, on the ICE device.

Figure 5B:
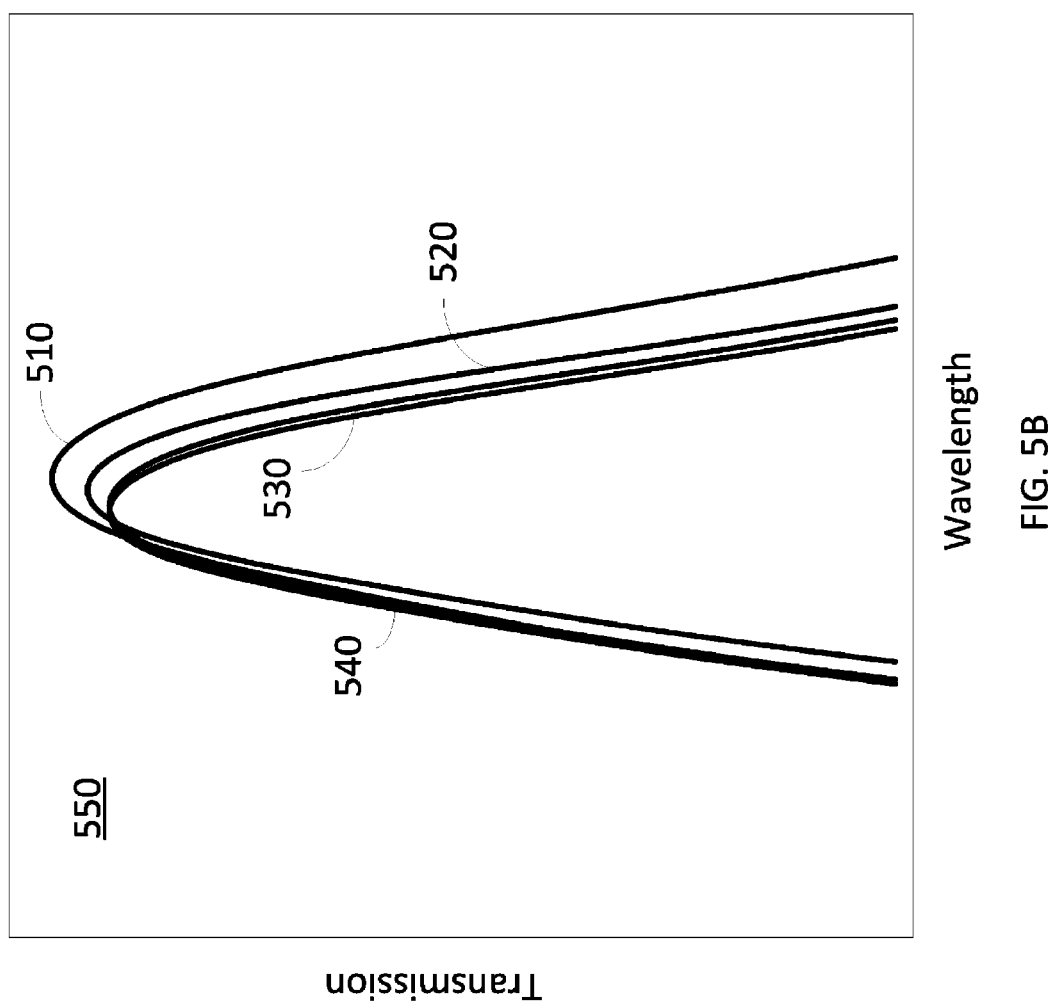
FIG. 5B illustrates a detailed view of a peak in the transmission spectra of FIG. 5A, according to some embodiments.

Referring to FIG. 5B, illustrated is an enlarged view of a peak 550 depicted in the transmission spectra of the plot 500 FIG. 5A, according to some embodiments. Peak 550 corresponds to the weighted spectra for peak 450 (cf. FIGS. 4A-4B).

In some embodiments, the ethane ICE device is modeled for a collimated optical beam. Accordingly, weighted spectrum 510 (angular distribution 302A) may closely represent the "true" regression vector for ethane. In this scenario, weighted spectrum 510 represents the best performance of an optical system for ethane measurements. Spectra 520, 530, and 540 are calculated for incident optical beams having angular distribution 302B, 302C, and 302D, respectively. For example, spectrum 520 corresponds to normal angular distribution 302B, which quickly falls to 0% as the angle of incidence approaches ±Δ (about 15°). The ICE device transmission spectrum corresponding to a given angle of incidence (cf. FIG. 4A) is multiplied ("weighted") by the density of rays at that angle of incidence according to angular distribution 302B (cf. FIG. 3). The weighted spectra for all angles in angular distribution 302B are added to yield weighted spectrum 520. Likewise, weighted spectra 510, 530 and 540 are obtained for a selected ICE device. In the example shown in FIG. 5A for an ethane ICE device, the largest spectral shift relative to the true ethane regression vector occurs for bimodal angular distribution 302D, which has a higher density of rays (about 7%) at near 8° from the normal. For an incident optical beam having a bimodal angular distribution, weighted spectrum 540 of an ICE device modeled for normal incidence has a blue shift of about 5 nm. Also, as shown in FIG. 5B, the mismatch includes decrease in transmitted intensity through the ICE device.

Weighted spectra 510, 520, 530, and 540 generally differ from the true ethane regression vector, as the shift in peak 550 shows. Assuming that spectra 510, corresponding to a nearly collimated optical beam having angular distribution 302A (cf. FIG. 3), is the closest representation of the true ethane regression vector, then weighted spectra 520, 530 and 540 deviate from the true regression vector accordingly. Irrespective of which one of weighted spectra 510, 520, 530 or 540 best represents the true ethane regression vector, a change in angular distribution of the incident optical beam introduces deviations in the performance of ICE device 100. Deviations in the performance of ICE device 100 are reflected in a consequent increase in SEC. Having detailed information of weighted spectra 510, 520, 530, and 540 and having detailed information of the true ethane regression vector, an estimate of the SEC value in each of the incident optical beams may be determined for a particular choice of ICE device 100. This determination is described in detail with reference to FIG. 6, below.

Figure 6:
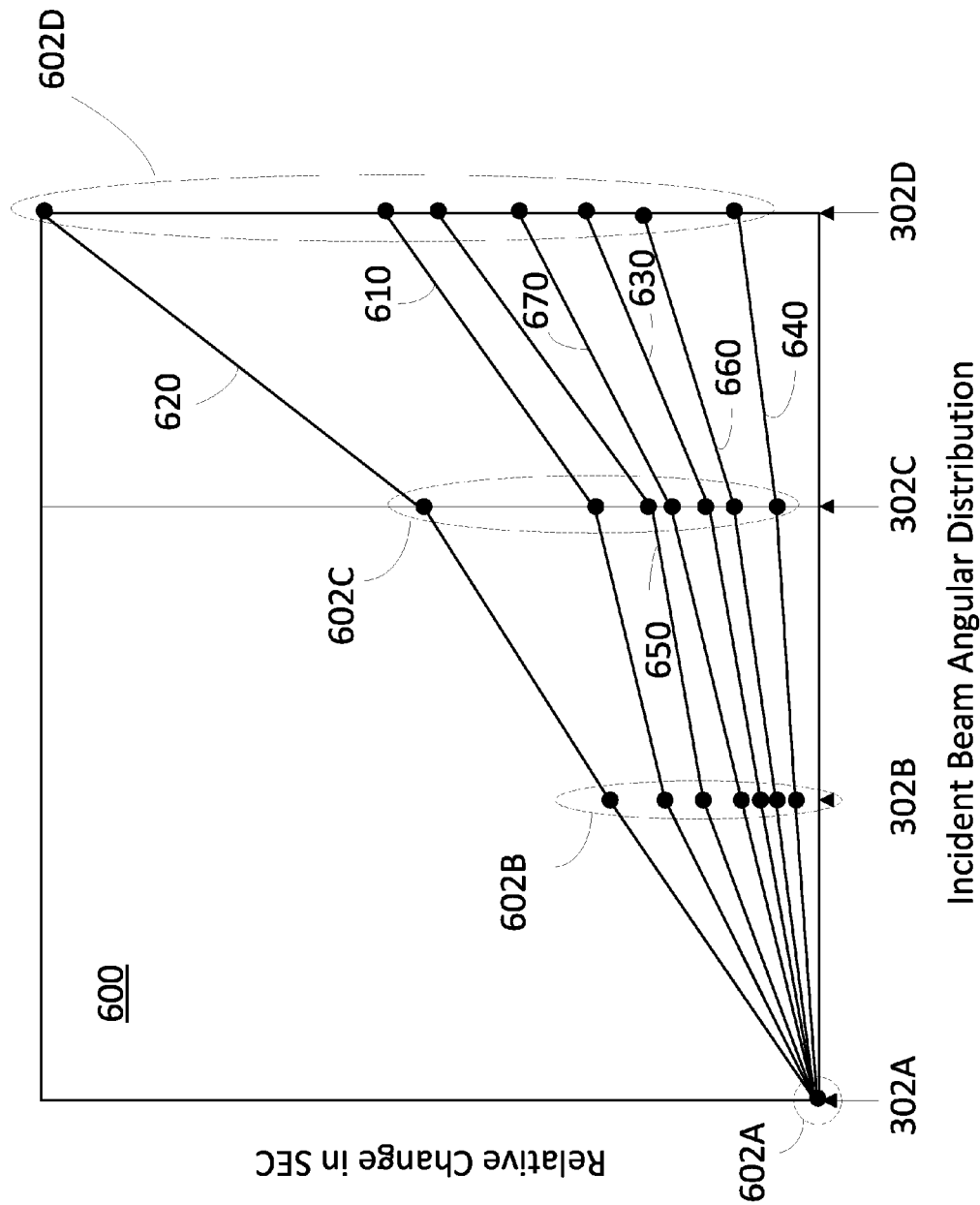
FIG. 6 illustrates a SEC plot to determine the sensitivity of a plurality of ICE devices to incident beams having different angular distribution, according to some embodiments.

FIG. 6 illustrates a SEC plot 600 to determine the sensitivity of a plurality of ICE devices to incident beams having different angular distribution, according to some embodiments. More specifically, FIG. 6 illustrates relative increase in SEC values corresponding to different angular distributions for seven (7) ethane ICE devices. Curve 610 corresponds to ICE device model '1'. Curve 620 corresponds to ICE device model '2'. Curve 630 corresponds to ICE device model '3'. Curve 640 corresponds to ICE device model '4'. Curve 650 corresponds to ICE device model '5'. Curve 660 corresponds to ICE device model '6', and Curve 670 corresponds to ICE device model '7'.

Table 1 below details the specific characteristics of the seven ethane ICE devices in FIG. 6. Each row in Table 1 represents an ethane ICE device that has been selected according to the true regression vector for ethane and assuming a collimated optical beam incident on the ICE device (e.g., with angular distribution close to 302A, cf. FIG. 1). Each column in Table 1 represents a layer of material. For example, the first column to the left in Table 1 may indicate thickness values for a high refractive index material layer (e.g., Si), and the second column may indicate thickness values for a low refractive index material layer (e.g., $SiO_2$). Material layers alternate as described in detail above (cf. FIG. 1).

shows a relSEC increase of less than 1% for each incident beam angular distribution 302A-D in ICE device '4'. Curve 620 shows a relSEC increase of more than 6% for the broadest angular distribution (302D) in ICE device '2'. Accordingly, an operator may choose ICE device no. 4 for fabrication when optical system robustness relative to the NA of incident optical beams is desirable.

One of ordinary skill will recognize that the ordinates in plot 600 may indicate any ICE device performance criteria other than, or in combination with SEC. For example, plot 600 may include a sensitivity or SNR in the ordinates. For example, a reduction in sensitivity may result from an increase in NA of the incident optical beam. Likewise, a reduction in SNR may result from an increase in NA of the incident optical beam. Accordingly, sensitivity and SNR can be used to select ICE device according to performance with respect to incident beam angular distribution. More generally, any combination of performance criteria as disclosed above may be used in the ordinates of plot 600 to select an ICE device model for fabrication.

Figure 7:
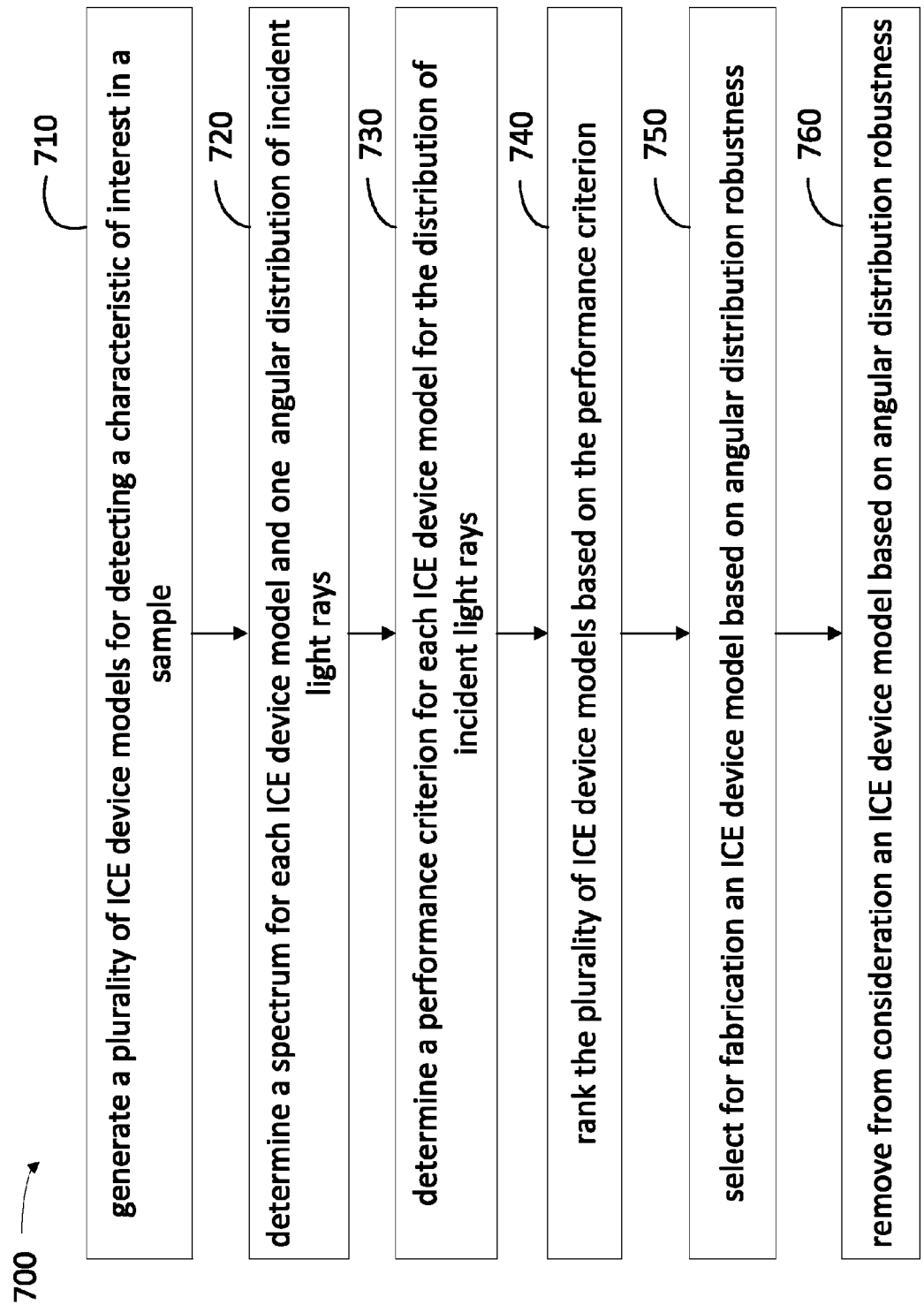
FIG. 7 illustrates a schematic flowchart of a method for evaluating an ICE device model for fabrication, according to one or more embodiments.

FIG. 7 illustrates a schematic flowchart of a method 700 for evaluating an ICE device for fabrication, according to one or more embodiments. An ICE device in method 700 may be included in an optical system having a high NA optical beam impinging on the ICE device (e.g., ICE device 100, optical system 200, optical beam 205, cf. FIG. 2). A high NA optical beam in method 700 may include light rays impinging on the ICE device with a broad angular distribution (e.g., angular distributions 302B-D, cf. FIG. 3). Steps in method 700 may be at least partially performed by an operator using a computing station, the computer station including a processor circuit and a memory circuit. Accordingly, the memory circuit may store instructions which, when executed by the processor circuit cause the computing

TABLE 1

| Design | Layer Thickness (nm) | | | | | | | | | | | |
|---|---|---|---|---|---|---|---|---|---|---|---|---|
| 1 | 1319.4 | 855.88 | 1037.8 | 610.57 | 1144.2 | 108.47 | 725.82 | — | — | — | — | — |
| 2 | 498.78 | 906.61 | 867.06 | 445.32 | 495.97 | 533.31 | 399.95 | 808.74 | 502.96 | — | — | — |
| 3 | 472.12 | 1287.2 | 1373.9 | 1325.1 | 293.31 | 756.95 | 906.49 | — | — | — | — | — |
| 4 | 507.93 | 387.73 | 613.14 | 569.4 | 291.63 | 257.86 | 937.45 | 625.23 | 182.85 | 540.29 | 629.46 | — |
| 5 | 1114.8 | 615.8 | 582.81 | 666.5 | 700.19 | 1089 | — | — | — | — | — | — |
| 6 | 176.2 | 136.34 | 418.91 | 226.72 | 365.12 | 52.04 | 547.9 | 483.17 | 396.77 | 463.99 | 32.9 | 698.2 |
| 7 | 415.13 | 985.33 | 748.67 | 882.66 | 385.29 | 332.7 | 685.55 | 1062 | — | — | — | — |

The ordinates in plot 600 (Y-axis) indicate a relative change in SEC for a given ethane ICE device. A relative change in SEC (relSEC) is calculated for each angular distribution 'i' with respect to angular distribution '1' as $$relSEC_i = (SEC_i/SEC_1) - 1 \qquad \text{Equation (1)}$$

For illustrative purposes, FIG. 6 shows results where angular distribution '1' corresponds to curve 302A and results in $relSEC_1$ data point 602A. Data point 602A is zero for all ICE devices, as can be seen by choosing i=1, in Equation (1) above. Angular distribution '2' corresponds to curve 302B and results in $relSEC_2$ data points 602B. Angular distribution '3' corresponds to curve 302C and results in $relSEC_3$ data points 602C, and angular distribution '4' corresponds to curve 302D and results in $relSEC_4$ data points 602D. FIG. 6 shows that relSEC increases for incident angular distributions where more light arrives at larger angles ('broader' angular distributions 302A-D, cf. FIG. 3). FIG. 6 also illustrates that the rate of increase in relSEC from a 'narrow' angular distribution to a 'broader' angular distribution is not the same for different ICE devices. Curve 640 station to perform at least some of the steps in method 700. Methods consistent with the present disclosure may include at least one of the steps in method 700, performed in any order. More generally, in some embodiments one or more of the steps in method 700 may be performed overlapping in time, or substantially at the same time. Some embodiments consistent with the present disclosure may include methods having additional steps to those illustrated in FIG. 7. Furthermore, some embodiments consistent with the present disclosure may include methods having some of the steps in FIG. 7 and not others. Methods disclosed herein may also help an operator to select an ICE device from a plurality of ICE device models resulting from processing within or otherwise with a design suite.

Step 710 includes generating a plurality of ICE device models for detecting a characteristic of interest in a sample. Step 710 may include using a processor circuit configured to execute commands from a design suite stored in a memory circuit. Step 710 may include determining a thickness of each alternating layer of material on a thin film stack and the number of layers to form the ICE device. Step 710 also includes comparing each ICE device model with a figure of merit, and selecting at least one model that satisfies the figure of merit. For example, step 710 may include forming a table with a list of models for ICE devices that satisfy the figure of merit (e.g., Table 1, including seven ICE device models). The figure of merit may be at least one of an absolute SEC, sensitivity, a SNR, a spectral overlap with a regression vector for a sample characteristic, or any combination of the above.

Step 720 includes determining a spectrum for each ICE device model and at least one angular distribution of incident light rays. The spectrum may be a weighted spectrum according to the angular distribution of incident light rays (e.g., spectra 510, 520, 530, and 540, cf. FIG. 5A). Accordingly, step 720 may include determining the angular distribution of incident light rays. For example, determining the angular distribution of light rays may include measuring the angular distribution in the optical system. In some embodiments, determining the angular distribution of incident light rays includes using a processor circuit executing commands from a ray propagation code stored in a memory circuit. Moreover, in some embodiments step 720 includes selecting the angular distribution of incident light rays to be generally broad (i.e., broader than a measured or calculated angular distribution). More specifically, step 720 may include determining an angular distribution of light rays impinging on a surface of an optical element where the ICE device may be deposited.

Step 730 includes determining a performance criterion for each ICE device model for the angular distribution of incident light rays. In some embodiments, step 730 includes determining a relative change in a SEC as the performance criterion. In other embodiments, step 730 includes determining at least one of a relative change in sensitivity and a relative change in SNR as a performance criterion. In yet other embodiments, step 730 includes determining an absolute value for the SEC, an absolute value of sensitivity, or an absolute value of SNR, as the performance criterion. Determining a performance criterion in step 730 may include selecting criteria from the group consisting of a minimum prediction error, standard error of prediction, slope of a calibration curve, and mean transmission value as tested against a known value for the characteristic of interest.

Step 740 includes ranking the plurality of ICE device models based on the performance criterion. For example, step 740 may include ranking ICE devices showing a lower increase in relative SEC with a higher mark than other ICE devices. In some embodiments, step 740 may include ranking ICE devices having a flat response in SEC with a higher mark than other ICE devices. Further, according to some embodiments, step 740 may include ranking ICE devices having a lower absolute SEC value with a higher mark than other ICE devices.

Step 750 includes selecting for fabrication an ICE device model based on angular distribution robustness. More particularly, step 750 may include selecting ICE device models having a higher mark in the ranking performed in step 740. For example, step 750 may include selecting the ICE device having the highest mark in the ranking of step 740. In other embodiments, step 750 includes selecting the ICE device model having a favorable angular tolerance. A favorable angular tolerance may be represented by ICE device model no. 4, for ethane (e.g., curve 640, cf. FIG. 6).

Step 760 includes removing from consideration ICE device models based on angular distribution robustness. For example, step 760 may include removing from consideration an ICE device having the lowest mark in the ranking of step 740. In other embodiments, step 760 comprises removing ICE device models based on poor performance criteria. A poor performance criterion may include ICE device model no. 2, for ethane (e.g., curve 620, cf. FIG. 6).

Those skilled in the art will readily appreciate that the methods described herein, or large portions thereof, may be automated at some point such that a computerized system may be programmed to design, predict, and fabricate ICE devices that are more robust for compact optical systems operating in extreme environments. Computer hardware used to implement the various methods and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method of designing an integrated computational element (ICE) device, comprising:
generating a plurality of ICE device models with a design suite stored on a non-transitory, computer-readable medium, each ICE device model comprising one or more layers and being configured to detect a characteristic of interest of a sample substance;
determining at least one transmission spectrum for each ICE device model for at least one distribution of incident light angles;
determining at least one performance criteria for each ICE device model for the at least one distribution of incident light angles;
ranking each ICE device model based on the at least one performance criteria of each ICE device model at the at least one distribution of incident light angles; and
selecting for fabrication one or more of the plurality of ICE device models based on favorable angular tolerance.

2. The method of claim 1, wherein the performance criteria comprises criteria selected from a group consisting of minimum prediction error, standard error of calibration, standard error of prediction, sensitivity, slope of a calibration curve, signal-to-noise ratio, and mean transmission value as tested against a known value for the characteristic of interest.

3. The method of claim 1, further comprising removing one or more of the plurality of ICE device models from consideration based on poor performance criteria.

4. The method of claim 1, wherein determining at least one transmission spectrum for each ICE device model for at least one distribution of incident light angles comprises weighting a spectrum of the ICE device model for a range of incident light angles.

5. The method of claim 1, wherein selecting for fabrication one or more of the plurality of ICE device models based on favorable angle tolerance comprises determining a weighted spectrum of the ICE device model for a range of incident light angles.

6. The method of claim 1, further comprising determining the at least one distribution of incident light angles for a compact optical system having a high numerical aperture optical beam.

7. A non-transitory, computer readable medium configured to store commands which, when executed by a processor circuit cause the processor circuit to:
generate a plurality of Integrated Computational Element (ICE) device models, each ICE device model targeted to measure a selected characteristic of a sample substance;
determine a spectrum for each ICE device model for at least one distribution of incident light angles;
determine a performance criterion for each ICE device model according to the at least one distribution of incident light angles;
rank the plurality of ICE device models based on the performance criterion; and
select for fabrication an ICE device model from the plurality of ICE device models based on a robustness for the at least one distribution of incident light angles.

8. The non-transitory, computer readable medium of claim 7, further comprising commands to cause the processor circuit to remove from consideration an ICE device model based on the robustness for the at least one distribution of incident light angles.

9. The non-transitory, computer readable medium of claim 7, wherein to determine the performance criterion for each ICE device model comprises to determine at least one of a relative standard error of calibration (SEC), a relative sensitivity, or a relative signal-to-noise ratio (SNR) for each ICE device model.

10. The non-transitory, computer readable medium of claim 7, wherein to determine the performance criterion for each ICE device model comprises to determine an absolute SEC, an absolute sensitivity, or an absolute SNR for each ICE device model.

11. The non-transitory, computer readable medium of claim 7, further comprising commands to cause the processor circuit to determine the at least one distribution of incident light angles.

12. The non-transitory, computer readable medium of claim 7, wherein to determine a spectrum for one of the ICE device models comprises to add a weighted sum of angular spectra, wherein the weighted sum is based on the at least one distribution of incident light angles.

13. The non-transitory, computer readable medium of claim 7, wherein to generate a plurality of ICE device models comprises generating at least one ICE device model based on a collimated array of incident light rays.

14. The non-transitory, computer readable medium of claim 7, wherein to rank the plurality of ICE device models based on the performance criterion comprises selecting a first ICE device model that is more tolerant to a broad distribution of incident light angles over a second ICE device model that is less tolerant to the broad distribution of incident light angles.

15. An optical system comprising:
a light source to provide an optical beam comprising a plurality of light rays;
an optical assembly to direct the optical beam to interact with a sample substance and thereby generate an interacted optical beam; and an integrated computational element (ICE) device to receive the interacted optical beam and direct at least a portion of the interacted optical beam to a detector, the portion of the interacted optical beam selected according to a regression vector for a characteristic of the sample substance, wherein the portion of the interacted optical beam directed to the detector includes light rays forming a large angle of incidence with a contact surface of the ICE device.

16. The optical system of claim 15, further comprising a high numerical aperture optical beam including the light rays forming a large angle of incidence with a contact surface of the ICE device.

17. The optical system of claim 15, wherein the optical assembly includes at least one of aspheric optical elements and diffractive optical elements.

18. The optical system of claim 15, wherein the ICE device is deposited on the surface of an element in the optical assembly.

19. The optical system of claim 15, wherein the regression vector for a characteristic of the sample substance varies less than a pre-determined amount for the light rays forming a large angle of incidence with a contact surface of the ICE device.

20. The optical system of claim 15, wherein the large angle of incidence is about 15° or more from the normal to the contact surface of the ICE device.

* * * * *